United States Patent
Klittich et al.

(10) Patent No.: US 6,815,556 B2
(45) Date of Patent: Nov. 9, 2004

(54) COMPOUNDS HAVING FUNGICIDAL ACTIVITY AND PROCESSES TO MAKE AND USE SAME

(75) Inventors: Carla Jean Rasmussen Klittich, Zionsville, IN (US); Jeannie Rachel Cetusic, Avon, IN (US); Marilene Tenguan Iamauti, Campinas (BR); Irene Mae Morrison, Indianapolis, IN (US); Michael Thomas Sullenberger, Westfield, IN (US); William Chi-Leung Lo, Fishers, IN (US); Ann Marie Buysse, Carmel, IN (US); Brent Jeffrey Rieder, Greenfield, IN (US); John Todd Mathieson, Brownsburg, IN (US); Monica Britt Olson, Lebanon, IN (US); Michael John Ricks, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/415,722

(22) PCT Filed: Nov. 16, 2001

(86) PCT No.: PCT/US01/44032
§ 371 (c)(1),
(2), (4) Date: Jun. 9, 2003

(87) PCT Pub. No.: WO02/40431
PCT Pub. Date: May 23, 2002

(65) Prior Publication Data
US 2004/0030189 A1 Feb. 12, 2004

Related U.S. Application Data

(60) Provisional application No. 60/249,653, filed on Nov. 17, 2000.

(51) Int. Cl.$^7$ .................. C07C 309/04; A01N 47/10
(52) U.S. Cl. .................. 560/12; 514/478; 514/479; 514/596; 514/597; 514/598; 514/546; 514/469; 514/522; 564/48; 564/49; 546/291; 546/292; 549/467; 558/413
(58) Field of Search .................. 560/12; 558/413; 564/48, 49; 546/291, 292; 549/467; 514/478, 479, 596, 597, 598, 546, 469, 522

(56) References Cited

U.S. PATENT DOCUMENTS 5,346,907 A * 9/1994 Kerwin et al. .............. 514/312

* cited by examiner

Primary Examiner—Shailendra Kumar
(74) Attorney, Agent, or Firm—Lynn M. Zettler; Carl D. Corvin

(57) ABSTRACT

A compound according to formula one that is useful as a fungicide is provided. Additionally, processes to make and use same are provided.

28 Claims, No Drawings

COMPOUNDS HAVING FUNGICIDAL ACTIVITY AND PROCESSES TO MAKE AND USE SAME

PRIORITY

This application is a 371 of PCT/US01/44032, filed Nov. 16, 2001, which claims benefit of 60/249,653, filed Nov. 17, 2000.

FIELD OF THE INVENTION

This invention is related to the field of compounds having fungicidal activity and processes to make and use such compounds.

BACKGROUND OF THE INVENTION

Our history is riddled with outbreaks of fungal diseases that have caused widespread human suffering. One need look no further than the Irish potato famine, which occurred from 1845 to 1860, where an estimated 1,000,000 people died, and an estimated 1,500,000 people emigrated, to see the effects of a fungal disease. Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop and consequently, increase the value of the crop. In most situations, the increase in value of the crop is worth at least three times the cost of the use of the fungicide. However, no one fungicide is useful in all situations. Consequently, research is being conducted to produce fungicides that are safer, that have better performance, that are easier to use, and that cost less. In light of the above, the inventors provide this invention.

SUMMARY OF THE INVENTION

It is an object of this invention to provide compounds that have fungicidal activity. It is an object of this invention to provide processes that produce compounds that have fungicidal activity. It is an object of this invention to provide processes that use compounds that have fungicidal activity. In accordance with this invention, processes to make and processes to use compounds having a general formula according to formula one, and said compounds are provided. While all the compounds of this invention have fungicidal activity, certain classes of compounds may be preferred for reasons such as, for example, greater efficacy or ease of synthesis.

Throughout this document, all temperatures are given in degrees Celsius and all percentages are weight percentages, except for percent yields which are mole percentages, unless otherwise stated. The term "alkyl", "alkenyl", or "alkynyl" refers to an unbranched, or branched, chain carbon group. The term "alkoxy" refers to an unbranched, or branched, chain alkoxy group. The term "haloalkyl" refers to an unbranched, or branched, alkyl group substituted with one or more halo atoms, defined as F, Cl, Br, and I. The term "haloalkoxy" refers to an unbranched, or branched, chain alkoxy group substituted with one or more halo atoms. The term "alkoxylalkyl" refers to an unbranched, or branched, chain alkyl group substituted with one or more alkoxy groups. The term "alkoxyalkoxy" refers to an unbranched, or branched, chain alkoxy group substituted with one or more alkoxy groups. The term "aryl" refers to a phenyl or naphthyl group. The term "Me" refers to a methyl group. The term "Et" refers to an ethyl group. The term "Pr" refers to a propyl group. The term "Bu" refers to a butyl group. The term "EtOAc" refers to ethyl acetate. The term "ppm" refers to parts per million. The term, "psi" refers to pounds per square inch.

Heteroaryl is defined by the following Formula Two

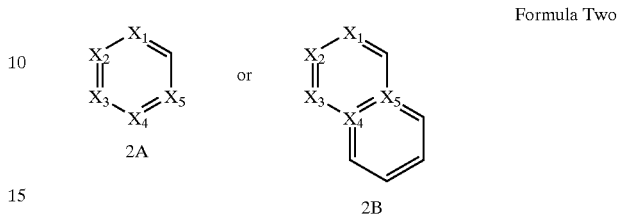

Formula Two wherein 2A represents a 5- or 6-membered ring and 2B represents a 9- or 10-membered fused bicyclic ring in which each of $X_1$–$X_5$ is independently a bond, O, S, $NR^7$, N, or CR, where R is selected from the group consisting of halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{1-4}$ alkoxyalkyl, $C_{1-4}$ alkoxyalkoxy, CN, $NO_2$, OH, SCN, $C(=O)R^6$, $C(=NR^6)R^6$, $S(O_n)R^6$ where n=0, 1 or 2, aryl, aryloxy, heteroaryl, and heteroaryloxy, and where no more than one of $X_1$–$X_5$ is O, S, or $NR^7$, no more than one of $X_1$–$X_5$ is a bond, when any one of $X_1$–$X_5$ is S, O or $NR^7$, one of the adjacent $X_1$–$X_5$ must represent a bond; and at least one of $X_1$–$X_5$ must be O, S, $NR^7$ or N.

Examples of such heteroaryls are pyridinyl, pyridazinyl, pyrimidinyl, pyrazinyl, pyrrolyl, pyrazolyl, imidazolyl, quinolinyl, isoquinolinyl, phthalazinyl, quinazolinyl, quinoxalinyl, cinnolinyl, indolyl, isoindolyl, indazolyl, thienyl, benzothienyl, furanyl, benzofuranyl, thiazolyl, benzothiazolyl, isothiazolyl, benzoisothiazolyls, oxazolyl, benzoxazolyl, isoxazolyl, and benzoisoxazolyl.

DETAILED DESCRIPTION OF THE INVENTION

The compounds of this invention have a formula according to formula one.

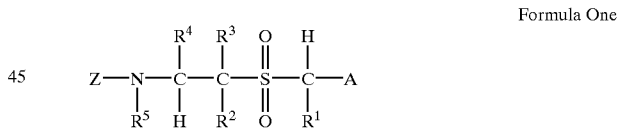

Formula One

In formula one:

$R^1$ is selected from the group consisting of F, Cl, Br, CN, $C_{1-4}$ alkyl, $C_{2-4}$ alkenyl, $C_{2-4}$ alkynyl, $C_{1-4}$ haloalkyl, $C_{1-4}$ alkoxyalkyl, $C_3$–$C_6$ cycloalkyl, $C_3$–$C_6$ cycloalkenyl, $CH_2(C(=O)R^5$, and $CH_2CN$;

$R^2$ and $R^3$ are selected from the group consisting of H, $CH_3$, F, and Cl;

$R^4$ is selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, aryl, and heteroaryl, where said alkyl, alkenyl, alkynyl, cycloalkyl, and cycloalkenyl, can be substituted with one or more substituents selected from the group consisting of halo, $C_{1-4}$ alkoxy, $C_{3-6}$ cycloalkyl, aryl and heteroaryl, and where said aryl and heteroaryl can be substituted with one or more substituents selected from the group consisting of halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{1-4}$ alkoxyalkyl, $C_{1-4}$ alkoxyalkoxy, CN, $NO_2$, OH, SCN, $C(=O)R^6$, $C(=NR^6)R^6$, $S(ON)R^6$ where n=0, 1 or 2, aryl, aryloxy, heteroaryl, and heteroaryloxy;

$R^5$ is selected from the group consisting of H, $OR^7$, and $C_{1-4}$ alkyl;

$R^6$ is selected from the group consisting of H, $C_{1-4}$ alkyl, $C_{2-4}$ alkenyl, $C_{2-4}$ alkynyl, $C_{1-4}$ haloalkyl, aryl, heteroaryl, $OR^7$, $N(R^7)_2$, and $SR^7$ where said aryl or heteroaryl can be substituted with one or more substituents selected from the group consisting of halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{1-4}$ alkoxyalkyl, CN, and $NO_2$;

$R^7$ is selected from the group consisting of H, $C_{1-4}$ alkyl, $C_{2-4}$ alkenyl, and $C_{2-4}$ alkynyl, $C_{1-4}$ haloalkyl, aryl, and heteroaryl, where said aryl or heteroaryl can be substituted with one or more substituents selected from the group consisting of halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{1-4}$ alkoxyalkyl, CN, and $NO_2$;

A is selected from the group consisting of aryl or heteroaryl, where said aryl and heteroaryl can be substituted with one or more substituents selected from the group consisting of halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{1-4}$ alkoxyalkyl, $C_{1-4}$ alkoxyalkoxy, CN, $NO_2$, OH, SCN, $C(=O)R^6$, $C(=NR^6)R^6$, $S(O_n)R^6$ where n=0, 1 or 2, aryl, aryloxy, substituted aryloxy, heteroaryl, and heteroaryloxy; and Z is selected from the group consisting of $C(=O)R^6$, $C(=S)R^6$, $P(=O)(R^6)_2$, and $P(=S)(R^6)_2$.

The compounds of Formula One have two chiral centers and can thus exist as mixtures of enantiomers and diastereomers. Where the stereochemistry is known, it is designated in the structure. This invention claims the pure enantiomers and diastereomers as well as the mixtures.

In general, these compounds can be used in a variety of ways. These compounds are preferably applied in the form of a formulation comprising one or more of the compounds with a phytologically acceptable carrier. Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of one or more of the compounds.

The formulations that are applied most often are aqueous suspensions or emulsions. Either such water-soluble, water suspendable, or emulsifiable formulations are solids, usually known as wettable powders, or liquids, usually known as emulsifiable concentrates, aqueous suspensions, or suspension concentrates. The present invention contemplates all vehicles by which one or more of the compounds can be formulated for delivery and use as a fungicide.

As will be readily appreciated, any material to which these compounds can be added may be used, provided they yield the desired utility without significant interference with the activity of these compounds as antifungal agents.

Wettable powders, which may be compacted to form water dispersible granules, comprise an intimate mixture of one or more of the compounds, an inert carrier and surfactants. The concentration of the compound in the wettable powder is usually from about 10% to about 90% w/w, more preferably about 25% to about 75% w/w. In the preparation of wettable powder formulations, the compounds can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the compounds in a volatile organic solvent. Effective surfactants, comprising from about 0.5% to about 10% of the wettable powder, include sulfonated lignins, naphthalenesulfonates, alkylbenzenesulfonates, alkyl sulfates, and nonionic surfactants, such as ethylene oxide adducts of alkyl phenols.

Emulsifiable concentrates of the compounds comprise a convenient concentration, such as from about 10% to about 50% w/w, in a suitable liquid. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface-active dispersing agents are usually employed in liquid formulations and in the amount of from 0.1 to 20 percent by weight of the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 50% w/w. Suspensions are prepared by finely grinding one or more of the compounds, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The compounds may also be applied as granular formulations, which are particularly useful for applications to the soil. Granular formulations usually contain from about 0.5% to about 10% w/w of the compounds, dispersed in an inert carrier which consists entirely or in large part of coarsely divided attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. Such formulations may also be prepared by making a dough or paste of the carrier and the compound, and crushing and drying to obtain the desired granular particle.

Dusts containing the compounds are prepared simply by intimately mixing one or more of the compounds in powdered form with a suitable dusty agricultural carrier, such as, for example, kaolin clay, ground volcanic rock, and the like. Dusts can suitably contain from about 1% to about 10% w/w of the compounds.

The formulations may contain adjuvant surfactants to enhance deposition, wetting and penetration of the compounds onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5%. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The formulations may optionally include combinations that can comprise at least 1% of one or more of the compounds with another pesticidal compound. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments the other pesticidal compound is employed as a supplemental toxicant for the same or for a different pesticidal use. The compounds and the pesticidal compound in the combination can generally be present in a weight ratio of from 1:100 to 100:1

The present invention includes within its scope methods for the control or prevention of fungal attack. These methods comprise applying to the locus of the fungus, or to a locus in which the infestation is to be prevented (for example applying to cereal or grape plants), a fungicidal amount of one or more of the compounds. The compounds are suitable for treatment of various plants at fungicidal levels, while exhibiting low phytotoxicity. The compounds are useful in a protectant or eradicant fashion. The compounds are applied by any of a variety of known techniques, either as the compounds or as formulations comprising the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds have been found to have significant fungicidal effect particularly for agricultural use. Many of the compounds are particularly effective for use with agricultural crops and horticultural plants, or with wood, paint, leather or carpet backing.

In particular, the compounds effectively control a variety of undesirable fungi that infect useful plant crops. Activity has been demonstrated for a variety of fungi, including for example the following representative fungi species: Downy Mildew of Grape (*Plasmopara viticola*—PLASVI); Late Blight of Tomato and Potato (*Phytophthora infestans*—PHYTIN); Brown Rust of Wheat (*Puccinia recondita*—PUCCRT); Powdery Mildew of Wheat (*Erysiphe graminis*—ERYSGT); Leaf Blotch of Wheat (*Septoria tritici*—SEPTTR); Sheath Blight of Rice (*Rhizoctonia solani*—RHIZSO); and Glume Blotch of Wheat (*Septoria nodorum*—LEPTNO). It will be understood by those in the art that the efficacy of the compound for the foregoing fungi establishes the general utility of the compounds as fungicides.

The compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease inhibiting and phytologically acceptable amount. The term "disease inhibiting and phytologically acceptable amount" refers to an amount of a compound that kills or inhibits the plant disease for which control is desired, but is not significantly toxic to the plant. This amount will generally be from about 1 to about 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.1 to 0.45 grams per square meter $g/m^2$).

EXAMPLES

These examples are provided to further illustrate the invention. They are not meant to be construed as limiting the invention.

Preparation of the Inventive Compounds

The claimed materials have been prepared by several methods that are described below. In general, the desired final product is prepared by the coupling of an electrophile with a sulfur nucleophile, followed by oxidation of the sulfur to the sulfone. The sulfur may be on either the amine half of the molecule or on the arylalkyl half, as shown in FIG. 1 below. The electrophilic and nucleophilic reactants may be prepared as shown in FIG. 1 by conventional methods well known to those skilled in the art.

(a. Carlson, R. M.; Lee, S. Y. *Tetrahedron Lett.* 1969, 4001. b. Rosenthal, D. et al. *J. Org. Chem.* 1965, 30, 3689. c. Mezo, G.; Mihala, N.; Koczan, B.; Hudecz, F. *Tetrahedron* 1998, 54, 6757. d. Boerner, A.; Voss, G. *Synthesis* 1990, 573.)

FIG. 1

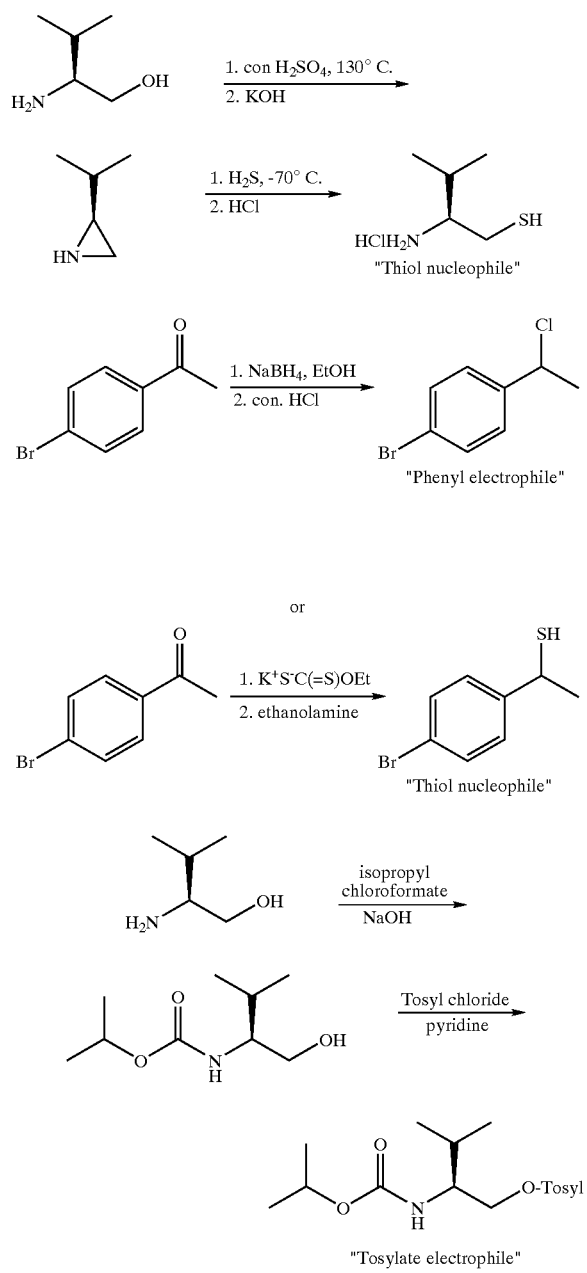

These two halves are coupled, the amine is acylated if necessary, and the sulfur is oxidized as is shown in FIG. 2

FIG. 2

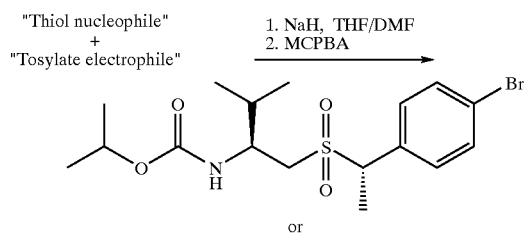

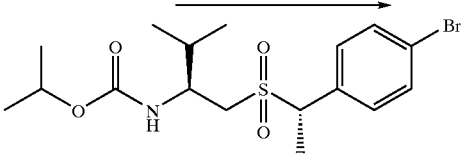

Preparation of Compound 21 by the Use of Thiol Nucleophile and Phenyl Electrophile A solution of 1.55 g of (S)-2-valinethiol nucleophile in 10 mL dry DMF was purged with nitrogen for 10 minutes. To this was added 20 mL of 1M potassium t-butoxide in THF, followed immediately by 2.20 g of the 1-(4-bromophenyl) chloroethane electrophile. The mixture was allowed to stir for 20 minutes, and then partitioned between water and ether/hexanes (1:1). The aqueous phase was extracted twice more and the organic phases washed with brine, dried, and solvent removed on the rotovap to give a pale oil. This could be purified by evaporative distillation, but was normally used as is. A solution of 1.21 g of the above crude product in 30 mL of dichloromethane was cooled in an ice bath and then a 20 mol % excess of 3-butyn-1-yl chloroformate (prepared by the action of 3 equivalents of phosgene as a 20% solution in toluene on the alcohol for 3–4 hours, followed by evaporation to remove toluene) was added, followed by 10 mL of saturated aqueous sodium bicarbonate solution. The two-phase mixture was vigorously stirred for 30 minutes, then the phases were separated, organic phase dried and diluted to 40 mL volume with dichloromethane. This was cooled in an ice bath, then 1.73 g m-chloroperbenzoic acid was added in portions with stirring, and the mixture stirred for 4–5 hours below 5° C. Sufficient 1.5M sodium thiosulfate solution was added to quench excess oxidant and then the mixture basicified with 2N sodium hydroxide. The phases were separated, and the organic phase dried, rotovapped, and the crude product purified by chromatography to give sulfone 21 as 1.42 g of white foam, 96% pure by GLC.

Preparation of Compound 4 by Use of Thiol Nucleophile and Tosylate Electrophile

A solution of 354 mg of 1-(4-trifluoromethoxyphenyl) ethanethiol was added to a nitrogen purged suspension of 1 equivalent of sodium hydride in 20 mL of dry tetrahydrofuran (THF) and stirred to give a clear solution. To this was added 500 mg of (S)-isopropoxycarbonylvalinol tosylate, and the mixture was stirred overnight at room temperature. The reaction was worked up and oxidized in the same manner as the method used for compound 21 above, purified by chromatography to give 269 mg white solid. MP 50–60° C.

By the above two methods, one can prepare most compounds of the type claimed, including compounds 1–43, except for compounds 11, 12, and 15 which were prepared from compound 1 by methods to be described below, and compound 22 whose preparation is also described below. The first described method is in general most useful.

The phenyl electrophiles used can be prepared as shown in FIG. 3.

FIG. 3

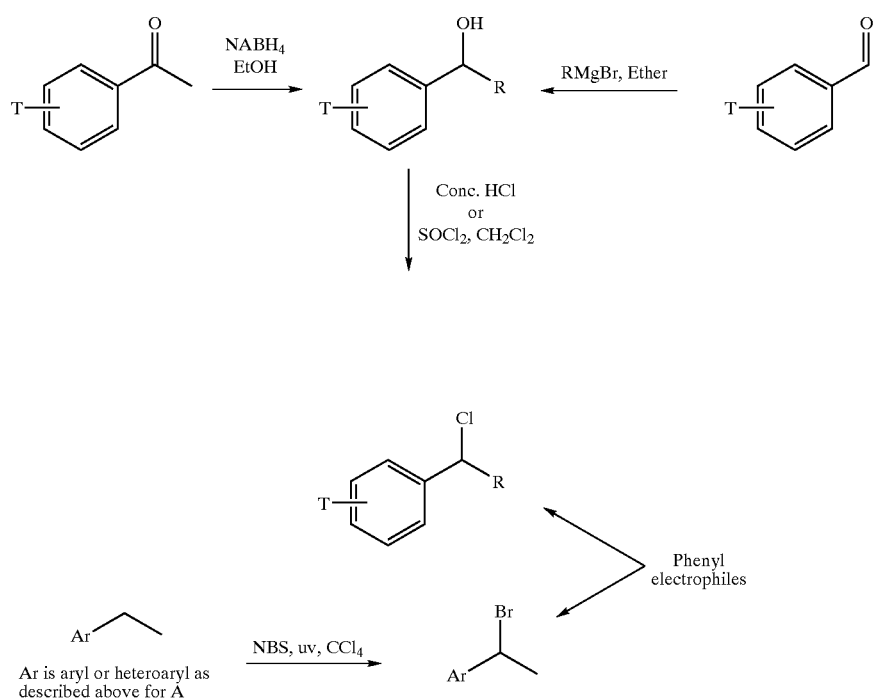

The reduction of acetophenones to alcohols and the conversion of these alcohols by either the use of concentrated hydrochloric acid neat or thionyl chloride in methylene chloride are well known by those practiced in the art. (Larock, R. C. *Comprehensive Organic Transformations: a Guide to Functional Group Preparations*; VCH Publishers, Inc.: New York, New York, 1989; p. 529, 354–355.) The electrophiles used to prepare compounds 1–43, (except for compounds 8, 10–12, 15, and 26) were prepared by this method.

The radical bromination of arylethanes using N-bromosuccinimide and UV light to make 1-bromo-1-arylethanes is also well known, (Djerassi, C; *Chem. Rev.* 1948, 43, 271) and this method was used to prepare electrophiles for compounds 8 and 10.

The phenyl electrophiles discussed above could be transformed into thiol nucleophiles by the well described use of xanthate salts as shown in FIG. 4. (Degani, I.; Fochi, R. *Synthesis* 1978, 365) These nucleophiles can be used with the tosylate electrophile to prepare many of the inventive materials.

FIG. 4

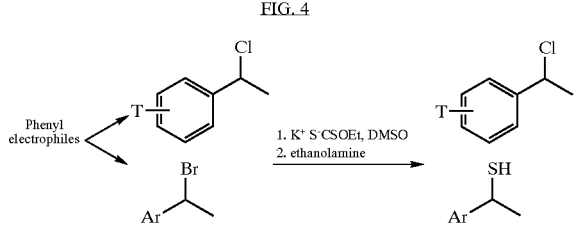

Compound 1 was converted into compound 11, and this material was used to prepare compounds 15 and 12 as shown in FIG. 5. All of the steps shown in FIG. 5 are well known to those in the art. (Morris, J.; Wishka, D. G. *J. Org. Chem.* 1991, 56, 3549.)

FIG. 5

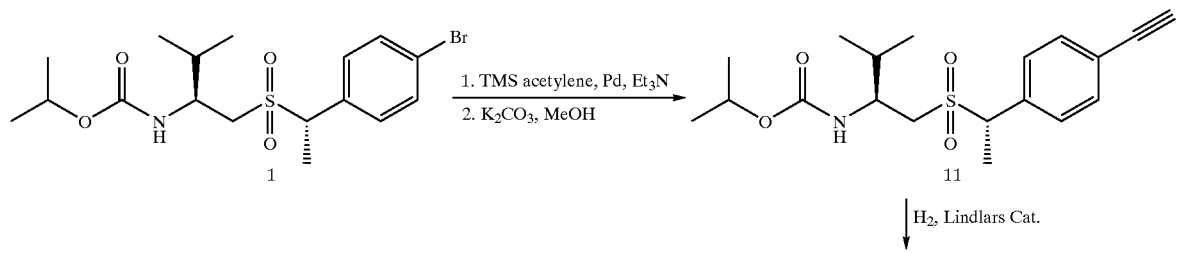

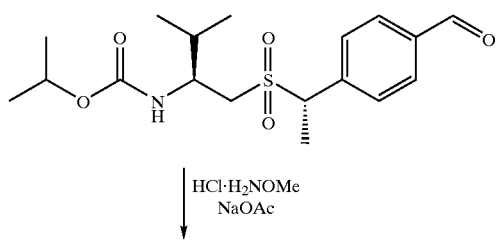

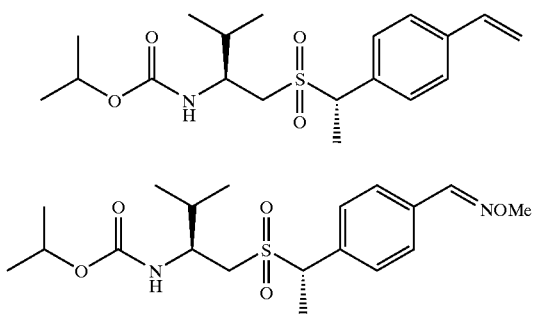

Compound 22 was prepared as shown in FIG. 6, and described in the preparation below.

FIG. 6

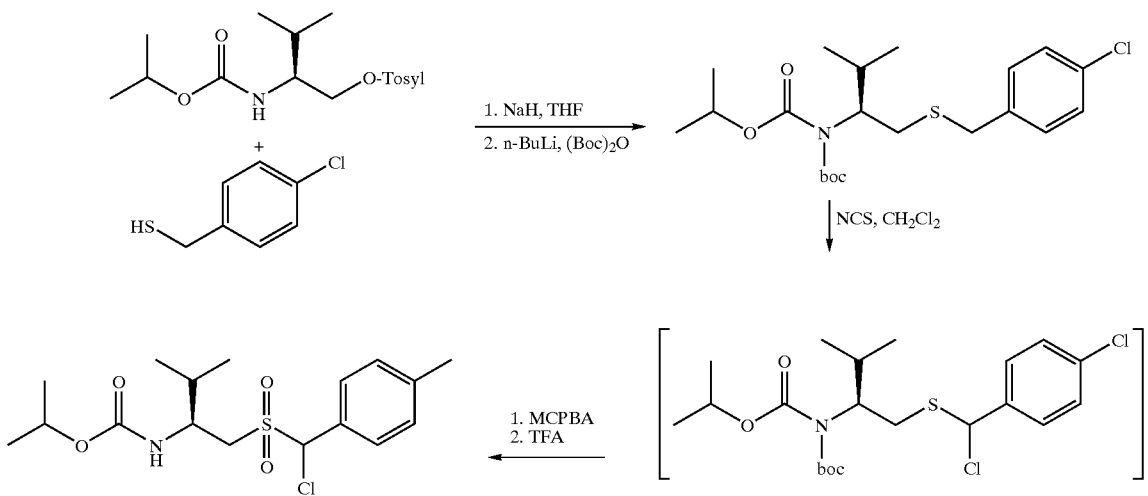

Preparation of isopropyl 1-({[chloro(4-chlorophenyl)methyl]sulfonyl}methyl)-2-methylpropylcarbamate (Compound 22)

To 88 mg of 60% sodium hydride in dry THF:DMF (4:1) under nitrogen atmosphere was added 350 mg of 4-chlorobenzylthiol, and the mixture stirred to give a clear solution. To this was added 686 mg of the tosylate electrophile, and the reaction was stirred for 3 hours at room temperature. The reaction was partitioned between 0.1N HCl and ether, aqueous extracted twice with ether, and the combined organic phases washed twice with brine. The ether phase was dried and evaporated, and the crude product purified by flash chromatography. To 385 mg of this material in 10 mL of dry THF at −78° C. was added 500 µL of 2.5M n-butyllithium in hexanes over 5 minutes, followed after 5 minutes by 281 mg of di-t-butyl dicarbonate in 2 mL of THF. The reaction was allowed to warm to room temperature and stirred for 4 hours, then worked up as above and the crude sulfide product purified by flash chromatography to give 245 mg of nearly colorless, viscous oil, pure by TLC and $^1$H NMR. To a solution of the above sulfide in 10 mL of methylene chloride, cooled in an ice-bath, was added a solution of 83 mg of N-chlorosuccinimide in 3 mL of methylene chloride over 5 minutes. The solution was stirred for 4 hours as it warmed to room temperature. To this solution was added 300 mg of MCPBA, and the reaction was stirred an additional 2 hours. The excess oxidant was quenched with sodium thiosulfate solution, then basified with 2N sodium hydroxide. The phases were separated, the organic phase was dried, and solvent removed on the rotovap. The residue was dissolved in 5 mL of methylene chloride and cooled to 10° C., and then 2 mL of TFA was added, followed by stirring overnight. The solvents were removed on the rotovap and the residue purified by flash chromatography to give 80 mg of a white solid.

Compound 26 was prepared using selective alkylation conditions on the sulfone shown in FIG. 7. (Wada, A.; Tode, C.; Hiraishi, S.; Tanaka, Y.; Ohfusa, T.; Ito, M. *Synthesis* 1995, 1107.) The BOC group was removed and replaced with an aromatic carbamate using procedures previously described.

FIG. 7

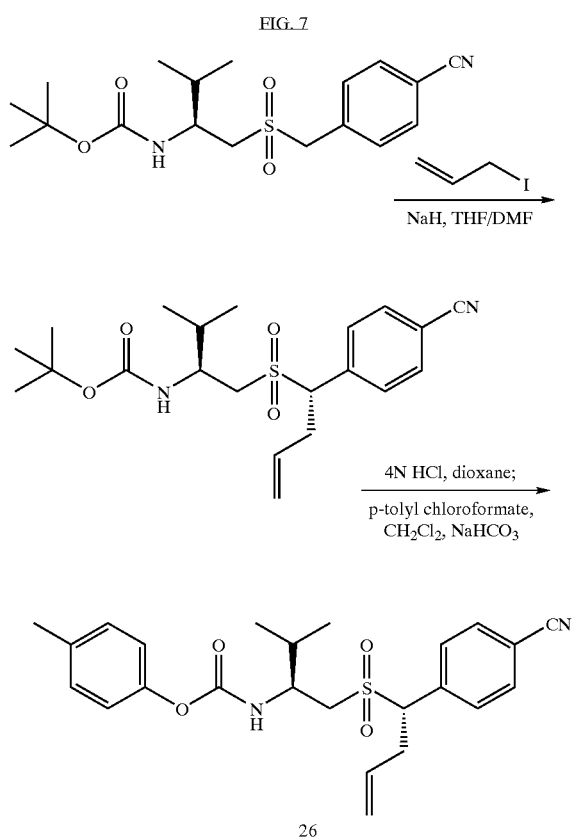

Compounds 32–34 were prepared by reaction of an isocyanate with the appropriate aromatic alcohol as shown in FIG. 8. (Blahak, J. *Ann. Chem.* 1978,1353.)

FIG. 8

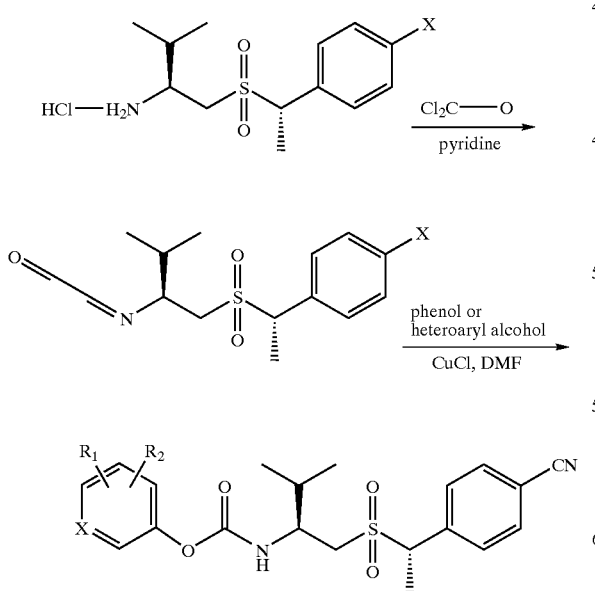

32: X = N, R$_1$ = H, R$_2$ = 4-OEt
33: X = C, R$_1$, R$_2$ = 3,4-diMe
34: X = C, R$_1$ = H, R$_2$ = 2-Br

Compound 37 was likewise generated from the amine salt and an appropriately substituted phenyl isocyanate as shown in FIG. 9. (Gaudry, R. *Can J. Chem.* 1951, 29, 544)

FIG. 9

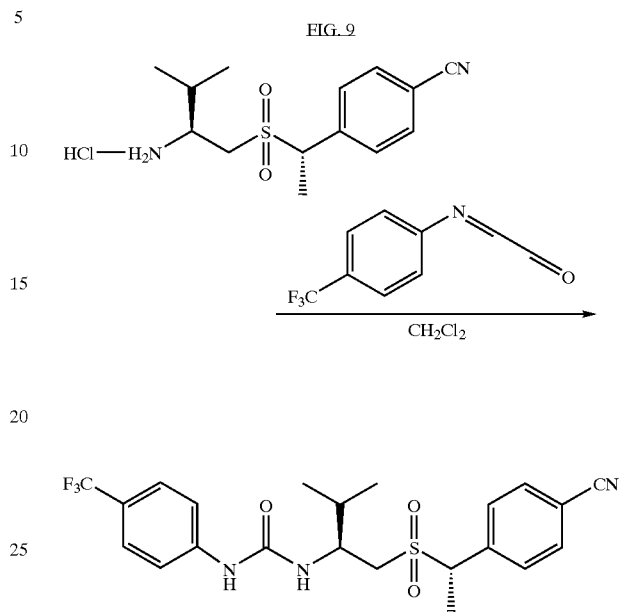

Compound 44 was prepared in 8 steps from valine methyl ester utilizing amino acid chemistry (a. Overhand, M.; Hecht, S. M. *J. Org. Chem.* 1994, 59, 4721. B. Son, Y. C.; Park, C. H.; Koh, J. S.; Choy, N. Y.; Lee, C. S.; Choi, H.; Kim, S. C.; Yoon, H. S. *Tetrahedron Lett.* 1994, 35, 3745. C. Nacci, V.; Campiani, G.; Garofalo, A. *Synth. Commun.* 1990, 20, 3019.) combined with coupling and oxidation chemistry described above.

FIG. 10

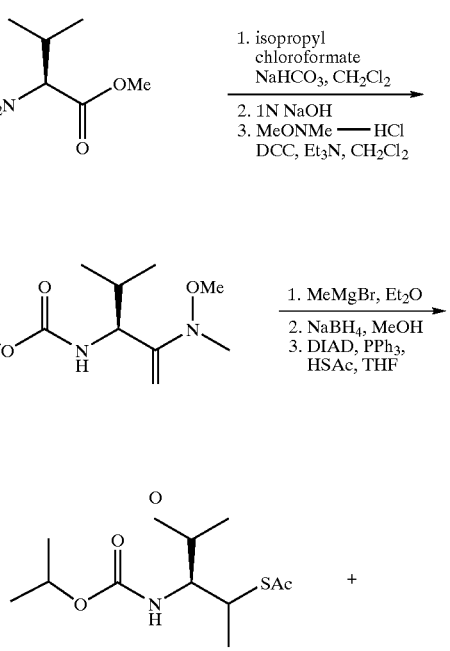

-continued

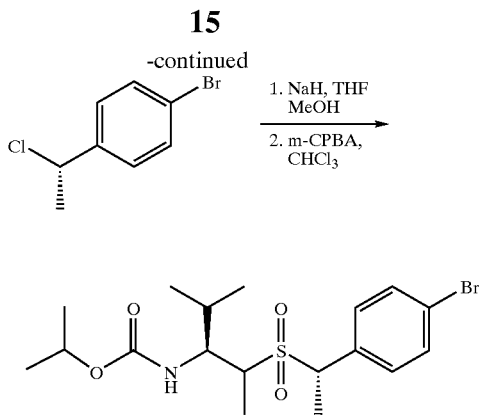

44

In Table 1, "EA" stands for elemental analysis.

TABLE 1

PHYSICAL DATA FOR SELECTED COMPOUNDS

| Compound Number | Physical state | MP | MS | NMR | EA |
|---|---|---|---|---|---|
| 1 | white solid | 60–70 | | X | X |
| 2 | white solid | 110–120 | | X | X |
| 3 | gum | | | | |
| 4 | white solid | 50–60 | | X | X |
| 5 | white solid | 75–85 | | X | X |
| 6 | tan solid | | 416 (M − 1) | | |
| 7 | white foam | | 416 (M − 1) | X | X |
| 8 | white foam | | | X | X |
| 9 | gum | | 371 (M − 1) | | |
| 10 | white solid | | | X | X |
| 11 | pale yellow solid | 125–135 | | X | X |
| 12 | sticky white foam | | | X | |
| 13 | white solid | | | X | X |
| 14 | white solid | 140–145 | | X | X |
| 15 | white solid | 50–60 | | X | X |
| 16 | tan solid | | 390 (M − 1) | | |
| 17 | white foam | 55–65 | | X | X |
| 18 | white foam | | 419 (M+) | X | |
| 19 | white foam | | 415 (M + 1) | X | X |
| 20 | clear glass | | | X | |
| 21 | white foam | | | X | X |
| 22 | white solid | 140–143 | | X | |
| 23 | viscous gum | | | X | X |
| 24 | off-white sticky solid | | 465 (M+) | X | |
| 25 | yellow foam | | | X | |
| 26 | colorless oil | | 441 (M+) | X | |
| 27 | white foam | | 457 (M + 1) | X | |
| 28 | white glass | | | X | X |
| 29 | white solid | 65–74 | 415 (M + 1) | X | X |
| 30 | white foam | | 479 (M + 1) | X | X |
| 31 | white powder | 129–135 | 504 (M + 1) | X | X |
| 32 | white solid | | 500/502 (M + 1) | X | |
| 33 | white foam | | 429 (M + 1) | X | X |
| 34 | white foam | | 480 (M + 1) | X | |
| 35 | yellow foam | | 383 (M + 1) | X | |
| 36 | clear glass | | 369 (M + 1) | X | |
| 37 | white glass | | 468 (M + 1) | X | X |
| 38 | white powder | 50–60 | 401 (M + 1) | X | |
| 39 | glass | | 435 (M + 1) | X | |
| 40 | waxy white solid | | 431 (M + 1) | X | |
| 41 | white crystals | 58–65 | | X | |
| 42 | white foam | 50–62 | 405 (M + 1) | X | |
| 43 | white foam | 50–53 | 431 (M + 1) | X | |
| 44 | clear oil | | 435 (M+) | X | |

Biological Testing

The compounds were formulated at 100 ppm in 10 vol % acetone plus 90 vol % Triton X water (deionized water 99.99 wt % +0.01 wt % Triton X100). The compounds were tested for ability to control plant diseases at the whole plant level in a 1-day protectant test (1 DP). Chemicals were sprayed on a turn table sprayer fitted with two opposing air atomization nozzles which delivered approximately 1500 L/ha of spray volume. Plants were inoculated with spores of the fungus the next day, then incubated in an environment conducive to disease development. Disease severity was evaluated 4 to 19 days later, depending on the speed of disease development.

The following experiments were performed in the laboratory to determine the fungicidal efficacy of the compounds of the invention.

Late Blight of Tomatoes (*Phytophthora infestans*—PHYTIN): Tomatoes (cultivar Rutgers) were grown from seed in a soilless peat-based potting mixture (Metromix) until the seedlings were 1–2 leaf (BBCH 12). These plants were then sprayed to run off with the formulated test compound at a rate of 100ppm. After 24 hours the test plants were inoculated with an aqueous spore suspension of *Phytophthora infestans* and incubated overnight in a dew chamber. The plants were then transferred to the greenhouse until disease developed on the untreated control plants.

Downy Mildew of Grapes (*Plasmopara viticola*—PLASVI): Grape plants (variety 'Carignane') were grown from seed in a greenhouse for six weeks in a soil-less potting mix until the seedlings were at a 2 to 3-leaf stage. These plants were sprayed to runoff with the formulated test compound at a rate of 100 ppm. After 24 hours the undersides of the leaves were inoculated with an aqueous spore suspension of *Plasmopara viticola* and the plants were kept in high humidity overnight. The plants were then transferred to a greenhouse until disease developed on untreated control plants.

Leaf Blotch of Wheat (*Septoria tritici*—SEPTTR): Wheat plants (variety Monon) were grown from seed in a greenhouse in 50% pasteurized soil/50% soil-less mix until the first true leaf was fully expanded, with 6–8 seedlings per pot. These plants were sprayed to runoff with the formulated test compound at a rate of 100 ppm. After 24 hours the leaves were inoculated with an aqueous spore suspension of *Septoria tritici* and the plants were kept in high humidity overnight. The plants were then transferred to a greenhouse until disease developed on untreated control plants.

The following table presents the activity of typical compounds of the present invention when evaluated in these experiments. The effectiveness of the test compounds in controlling disease was rated by giving the percent control of the plant disease compared with untreated, inoculated plants.

TABLE 2
Fungicidal activity of compounds on plant diseases in greenhouse tests.
Ratings are percent control in a one-day protectant test.
(− ≦20%, + = 20–49%, ++ = 50–89%, +++ = 90–100%, NT = not tested).
| Compound Number | Compound | PHYTIN | PLASVI | SEPTTR |
|---|---|---|---|---|
| 1 | 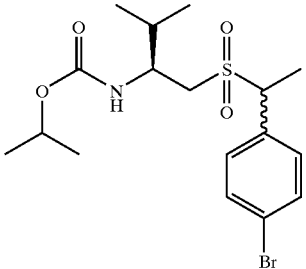 | +++ | +++ | − |
| 2 | 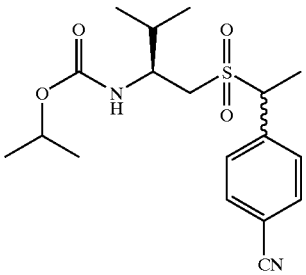 | +++ | +++ | − |
| 3 | 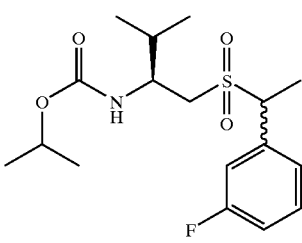 | +++ | ++ | NT |
| 4 | 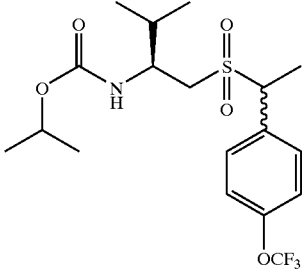 | +++ | +++ | − |
| 5 | 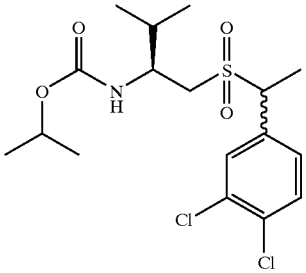 | +++ | ++ | − |

TABLE 2-continued

Fungicidal activity of compounds on plant diseases in greenhouse tests.
Ratings are percent control in a one-day protectant test.
(− ≦20%, + = 20–49%, ++ = 50–89%, +++ = 90–100%, NT = not tested).

| Compound Number | Compound | PHYTIN | PLASVI | SEPTTR |
|---|---|---|---|---|
| 6 | | +++ | +++ | NT |
| 7 | | +++ | ++ | + |
| 8 | | ++ | ++ | − |
| 9 | | +++ | +++ | NT |

TABLE 2-continued

Fungicidal activity of compounds on plant diseases in greenhouse tests.
Ratings are percent control in a one-day protectant test.
(− ≦20%, + = 20–49%, ++ = 50–89%, +++ = 90–100%, NT = not tested).

| Compound Number | Compound | PHYTIN | PLASVI | SEPTTR |
|---|---|---|---|---|
| 10 | (structure: isopropyl carbamate with isobutyl group, sulfone, linked to 6-bromobenzothiazol-2-yl via CH(CH3)) | +++ | +++ | NT |
| 11 | (structure: isopropyl carbamate with isobutyl group, sulfone, linked to 4-ethynylphenyl via CH(CH3)) | +++ | ++ | ++ |
| 12 | (structure: isopropyl carbamate with isobutyl group, sulfone, linked to 4-(MeON=CH)phenyl via CH(CH3)) | +++ | +++ | NT |
| 13 | (structure: isopropyl carbamate with isobutyl group, sulfone, linked to 4-nitrophenyl via CH(CH3)) | +++ | +++ | − |

TABLE 2-continued

Fungicidal activity of compounds on plant diseases in greenhouse tests.
Ratings are percent control in a one-day protectant test.
(− ≦20%, + = 20–49%, ++ = 50–89%, +++ = 90–100%, NT = not tested).

| Compound Number | Compound | PHYTIN | PLASVI | SEPTTR |
|---|---|---|---|---|
| 14 | [isopropyl carbamate with sulfonyl linked to 4-CO₂Me phenyl] | +++ | +++ | NT |
| 15 | [isopropyl carbamate with sulfonyl linked to 4-CHO phenyl] | +++ | +++ | NT |
| 16 | [isopropyl carbamate with sulfonyl linked to 2-naphthyl] | +++ | ++ | NT |
| 17 | [phenyl carbamate with sulfonyl linked to 4-Br phenyl] | +++ | +++ | + |
| 18 | [4-F-phenyl carbamate with sulfonyl linked to 4-CN phenyl] | +++ | +++ | ++ |

TABLE 2-continued

Fungicidal activity of compounds on plant diseases in greenhouse tests.
Ratings are percent control in a one-day protectant test.
(− ≦20%, + = 20–49%, ++ = 50–89%, +++ = 90–100%, NT = not tested).

| Compound Number | Compound | PHYTIN | PLASVI | SEPTTR |
|---|---|---|---|---|
| 19 | | +++ | +++ | NT |
| 20 | | +++ | ++ | + |
| 21 | | +++ | ++ | ++ |
| 22 | | +++ | +++ | − |
| 23 | | ++ | ++ | ++ |

TABLE 2-continued

Fungicidal activity of compounds on plant diseases in greenhouse tests.
Ratings are percent control in a one-day protectant test.
(- ≦20%, + = 20–49%, ++ = 50–89%, +++ = 90–100%, NT = not tested).

| Compound Number | Compound | PHYTIN | PLASVI | SEPTTR |
|---|---|---|---|---|
| 24 | | +++ | +++ | NT |
| 25 | | +++ | +++ | NT |
| 26 | | +++ | +++ | NT |
| 27 | | +++ | +++ | ++ |
| 28 | | +++ | +++ | NT |

TABLE 2-continued

Fungicidal activity of compounds on plant diseases in greenhouse tests.
Ratings are percent control in a one-day protectant test.
(− ≦20%, + = 20–49%, ++ = 50–89%, +++ = 90–100%, NT = not tested).

| Compound Number | Compound | PHYTIN | PLASVI | SEPTTR |
|---|---|---|---|---|
| 29 | (4-methylphenyl carbamate of isopropyl-CH₂-SO₂-CH(CH₃)-(4-cyanophenyl)) | +++ | +++ | ++ |
| 30 | (4-bromophenyl carbamate of isopropyl-CH₂-SO₂-CH(CH₃)-(4-cyanophenyl)) | +++ | +++ | NT |
| 31 | (2-naphthyl carbamate of isopropyl-CH₂-SO₂-CH(CH₃)-(4-bromophenyl)) | +++ | +++ | NT |
| 32 | (6-ethoxypyridin-3-yl carbamate of isopropyl-CH₂-SO₂-CH(CH₃)-(4-bromophenyl)) | +++ | +++ | NT |
| 33 | (3,4-dimethylphenyl carbamate of isopropyl-CH₂-SO₂-CH(CH₃)-(4-cyanophenyl)) | +++ | +++ | NT |

TABLE 2-continued

Fungicidal activity of compounds on plant diseases in greenhouse tests.
Ratings are percent control in a one-day protectant test.
(− ≦20%, + = 20–49%, ++ = 50–89%, +++ = 90–100%, NT = not tested).

| Compound Number | Compound | PHYTIN | PLASVI | SEPTTR |
|---|---|---|---|---|
| 34 | [structure] | +++ | +++ | NT |
| 35 | [structure] | +++ | +++ | NT |
| 36 | [structure] | ++ | ++ | NT |
| 37 | [structure] | +++ | +++ | NT |
| 38 | [structure] | +++ | +++ | NT |

TABLE 2-continued

Fungicidal activity of compounds on plant diseases in greenhouse tests.
Ratings are percent control in a one-day protectant test.
(− ≦20%, + = 20–49%, ++ = 50–89%, +++ = 90–100%, NT = not tested).

| Compound Number | Compound | PHYTIN | PLASVI | SEPTTR |
|---|---|---|---|---|
| 39 | (structure) | +++ | +++ | NT |
| 40 | (structure) | +++ | +++ | NT |
| 41 | (structure) | ++ | +++ | NT |
| 42 | (structure) | +++ | +++ | NT |

TABLE 2-continued

Fungicidal activity of compounds on plant diseases in greenhouse tests.
Ratings are percent control in a one-day protectant test.
(− ≦20%, + = 20–49%, ++ = 50–89%, +++ = 90–100%, NT = not tested).

| Compound Number | Compound | PHYTIN | PLASVI | SEPTTR |
|---|---|---|---|---|
| 43 | 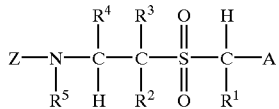 | ++ | +++ | NT |
| 44 | | +++ | ++ | NT |

We claim:

1. A compound according to formula one

Formula One $$Z-\underset{R^5}{\underset{|}{N}}-\underset{H}{\overset{R^4}{\underset{|}{C}}}-\underset{R^2}{\overset{R^3}{\underset{|}{C}}}-\underset{\underset{O}{\overset{||}{S}}}{\overset{O}{\underset{||}{S}}}-\underset{R^1}{\overset{H}{\underset{|}{C}}}-A$$

wherein:

$R^1$ is selected from the group consisting of F, Cl, Br, CN, $C_{1-4}$ alkyl, $C_{2-4}$ alkenyl, $C_{2-4}$ alkynyl, $C_{1-4}$ haloalkyl, $C_{1-4}$ alkoxyalkyl, $C_{3}$–$C_{6}$ cycloalkyl, $C_{3}$–$C_{6}$ cycloalkenyl, $CH_2(C=O)R^5$, and $CH_2CN$;

$R^2$ and $R^3$ are selected from the group consisting of H, $CH_3$, F, and Cl;

$R^4$ is selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, aryl, and heteroaryl, where said alkyl, alkenyl, alkynyl, cycloalkyl, and cycloalkenyl, can be substituted with one or more substituents selected from the group consisting of halo, $C_{1-4}$ alkoxy, $C_{3-6}$ cycloalkyl, aryl and heteroaryl, and where said aryl and heteroaryl can be substituted with one or more substituents selected from the group consisting of halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{1-4}$ alkoxyalkyl, CN, $NO_2$, OH, SCN, $C(=O)R^6$, $C(=NR^6)R^6$, $S(O_n)R^6$ where n=0, 1 or 2, aryl, aryloxy, heteroaryl, and heteroaryloxy;

$R^5$ is selected from the group consisting of H, $OR^7$, and $C_{1-4}$ alkyl;

$R^6$ is selected from the group consisting of H, $C_{1-4}$ alkyl, $C_{2-4}$ alkenyl, $C_{2-4}$ alkynyl, $C_{1-4}$ alkoxy, $C_{1-4}$ haloalkyl, aryl, heteroaryl, $OR^7$, $N(R^7)_2$, and $SR^7$ where said aryl or heteroaryl can be substituted with one or more substituents selected from the group consisting of halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{1-4}$ alkoxyalkyl, CN, and $NO_2$;

$R^7$ is selected from the group consisting of H, $C_{1-4}$ alkyl, $C_{2-4}$ alkenyl, $C_{2-4}$ alkynyl, $C_{1-4}$ haloalkyl, aryl and heteroaryl, where said aryl or heteroaryl can be substituted with one or more substituents selected from the group consisting of halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{1-4}$ alkoxyalkyl, CN, and $NO_2$;

A is selected from the group consisting of aryl or heteroaryl, where said aryl and heteroaryl can be substituted with one or more substituents selected from the group consisting of halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, $C_{1-4}$ alkoxyalkyl, $C_{1-4}$ alkoxyalkoxy, CN, $NO_2$, OH, SCN, $C(=O)R^6$, $C(=NR^6)R^6$, $S(O_n)R^6$ where n=0, 1 or 2, aryl, aryloxy, substituted aryloxy, heteroaryl, and heteroaryloxy; and Z is selected from the group consisting of $C(=O)R^6$, $C(=S)R^6$, $P(=O)(R^6)_2$, and $P(=S)(R^6)_2$.

2. A compound according to claim 1 wherein:

$R^1$ is selected from the group consisting of Cl, $C_{1-4}$ alkyl, and $C_{2-4}$ alkenyl;

$R^2$ and $R^3$ are selected from the group consisting of H and $CH_3$;

$R^4$ is a $C_{1-6}$ alkyl where said alkyl, can be substituted with one or more $C_{1-4}$ alkoxy substituents;

$R^5$ is H;

$R^6$ is selected from the group consisting of H, $C_{1-4}$ alkoxy, $OR^7$, $N(R^7)_2$, and $SR^7$;

R⁷ is selected from the group consisting of H, $C_{1-4}$ alkyl, $C_{2-4}$ alkenyl, $C_{2-4}$ alkynyl, $C_{1-4}$ haloalkyl, aryl, and heteroaryl, where said aryl or heteroaryl can be substituted with one or more substituents selected from the group consisting of halo, CN, $C_{1-4}$ alkyl, and $C_{1-4}$ alkoxy;

A is selected from the group consisting of aryl or heteroaryl, where said aryl and heteroaryl can be substituted with one or more substituents selected from the group consisting of halo, CN, $C_{1-4}$ alkoxy, $C_{1-4}$ haloalkoxy, aryl, substituted aryloxy, $C_{2-4}$ alkenyl, $C(=NR^6)R^6$, $NO_2$, and $C(=O)R^6$; and Z is selected from the group consisting of $C(=O)R^6$ and $C(=S)R^6$.

3. A compound according to claim 2 wherein:

A is selected from the group consisting of aryl or heteroaryl, where said aryl and heteroaryl is substituted with one substituent selected from the group consisting of Br and CN; and Z is selected from the group consisting of isopropyl and $C(=O)R^6$, where said $R^6$ is $OR^7$, and where said $R^7$ is selected from the group consisting of aryl and heteroaryl, where said aryl or heteroaryl is substituted with one substituent selected from the group consisting of halo and methyl.

4. A compound according to claim 3 wherein the substituent on A is in the para position and wherein Z is $C(=O)R^6$, where said $R^6$ is $OR^7$, and where said $R^7$ is selected from the group consisting of aryl and heteroaryl, where said aryl or heteroaryl is substituted with one substituent selected from the group consisting of halo and methyl, which is in the para position.

5. A compound according to claim 1 wherein:

$R^1$ is selected from the group consisting of Cl and methyl;

$R^2$ and $R^3$ is H;

$R^4$ is a $C_{1-6}$ alkyl;

$R^5$ is H;

$R^6$ is selected from the group consisting of H, methoxy, and $OR^7$;

$R^7$ is selected from the group consisting of $C_{1-4}$ alkyl, $C_{2-4}$ alkynyl, aryl where said aryl can be substituted with one or more substituents selected from the group consisting of halo and methyl;

A is selected from the group consisting of aryl or heteroaryl, where said aryl and heteroaryl can be substituted with one or more substituents selected from the group consisting of halo, CN, $C_{1-4}$ alkoxy, $C_{1-4}$ haloalkoxy, aryl, substituted aryloxy, $C_{2-4}$ alkynyl, $C(=NR^6)R^6$, $NO_2$, and $C(=O)R^6$; and Z is $C(=O)R^6$ where said $R^6$ is $OR^7$.

6. A compound according to claim 5 wherein:

A is selected from the group consisting of aryl or heteroaryl, where said aryl and heteroaryl is substituted with one substituent selected from the group consisting of Br and CN; and Z is selected from the group consisting of isopropyl and $C(=O)R^6$ where said $R^6$ is $OR^7$, and where said $R^7$ is selected from the group consisting of aryl and heteroaryl, where said aryl or heteroaryl is substituted with one substituent selected from the group consisting of halo and methyl.

7. A compound according to claim 6 wherein the substituent on A is in the para position and wherein Z is $C(=O)R^6$, where said $R^6$ is $OR^7$, and where said $R^7$ is selected from the group consisting of aryl and heteroaryl, where said aryl or heteroaryl is substituted with one substituent selected from the group consisting of halo and methyl, which is in the para position.

8. A process to control or prevent a fungal attack said process comprising applying to a locus a fungicidal amount of one or more of the compounds according to claim 1.

9. A process to control or prevent a fungal attack said process comprising applying to a locus a fungicidal amount of one or more of the compounds according to claim 2.

10. A process to control or prevent a fungal attack said process comprising applying to a locus a fungicidal amount of one or more of the compounds according to claim 3.

11. A process to control or prevent a fungal attack said process comprising applying to a locus a fungicidal amount of one or more of the compounds according to claim 4.

12. A process to control or prevent a fungal attack said process comprising applying to a locus a fungicidal amount of one or more of the compounds according to claim 5.

13. A process to control or prevent a fungal attack said process comprising applying to a locus a fungicidal amount of one or more of the compounds according to claim 6.

14. A process to control or prevent a fungal attack said process comprising applying to a locus a fungicidal amount of one or more of the compounds according to claim 7.

15. A composition comprising a disease inhibiting and phytologically acceptable amount of a compound according to claim 1 and at least one additional pesticidal compound selected from the group consisting of fungicides, insecticides, nematocides, miticides, arthropodicides, and bactericides.

16. A composition comprising a disease inhibiting and phytologically acceptable amount of a compound according to claim 2 and at least one additional pesticidal compound selected from the group consisting of fungicides, insecticides, nematocides, miticides, arthropodicides, and bactericides.

17. A composition comprising a disease inhibiting and phytologically acceptable amount of a compound according to claim 3 and at least one additional pesticidal compound selected from the group consisting of fungicides, insecticides, nematocides, miticides, arthropodicides, and bactericides.

18. A composition comprising a disease inhibiting and phytologically acceptable amount of a compound according to claim 4 and at least one additional pesticidal compound selected from the group consisting of fungicides, insecticides, nematocides, miticides, arthropodicides, and bactericides.

19. A composition comprising a disease inhibiting and phytologically acceptable amount of a compound according to claim 5 and at least one additional pesticidal compound selected from the group consisting of fungicides, insecticides, nematocides, miticides, arthropodicides, and bactericides.

20. A composition comprising a disease inhibiting and phytologically acceptable amount of a compound according to claim 6 and at least one additional pesticidal compound selected from the group consisting of fungicides, insecticides, nematocides, miticides, arthropodicides, and bactericides.

21. A composition comprising a disease inhibiting and phytologically acceptable amount of a compound according to claim 7 and at least one additional pesticidal compound selected from the group consisting of fungicides, insecticides, nematocides, miticides, arthropodicides, and bactericides.

22. A process comprising reacting the appropriate electrophile with the appropriate sulfur nucleophile to produce a compound according to claim 1.

23. A process comprising reacting the appropriate electrophile with the appropriate sulfur nucleophile to produce a compound according to claim 2.

24. A process comprising reacting the appropriate electrophile with the appropriate sulfur nucleophile to produce a compound according to claim 3.

25. A process comprising reacting the appropriate electrophile with the appropriate sulfur nucleophile to produce a compound according to claim 4.

26. A process comprising reacting the appropriate electrophile with the appropriate sulfur nucleophile to produce a compound according to claim 5.

27. A process comprising reacting the appropriate electrophile with the appropriate sulfur nucleophile to produce a compound according to claim 6.

28. A process comprising reacting the appropriate electrophile with the appropriate sulfur nucleophile to produce a compound according to claim 7.

* * * * *